US005388079A

United States Patent [19]

Kim et al.

[11] Patent Number: 5,388,079

[45] Date of Patent: Feb. 7, 1995

[54] PARTIAL BEAMFORMING

[75] Inventors: Jin Kim, Issaquah; Lin X. Yao, Bellevue; Zoran Banjanin, Renton, all of Wash.; Hiroshi Fukukita, Tokyo, Japan; Hisashi Hagiwara, Japan; Masami Kawabuchi, both of Yokohama, Japan

[73] Assignee: Siemens Medical Systems, Inc., Iselin, N.J.

[21] Appl. No.: 38,572

[22] Filed: Mar. 26, 1993

[51] Int. Cl.[6] .......................... G01S 15/00; A61B 8/00

[52] U.S. Cl. ................................ 367/103; 128/661.01

[58] Field of Search ............................... 367/103, 119; 128/661.01; 73/625, 626

[56] References Cited

U.S. PATENT DOCUMENTS

| | | | |
|---|---|---|---|
| 4,796,236 | 1/1989 | Welles, II et al. | 367/7 |
| 4,800,891 | 1/1989 | Kim | 128/661.09 |
| 5,191,546 | 3/1993 | Green | 364/723 |
| 5,217,017 | 6/1993 | Matsushima | 128/661.01 |
| 5,263,483 | 11/1993 | Nishigaki et al. | 128/660.01 |
| 5,268,877 | 12/1993 | Odell | 367/103 |

OTHER PUBLICATIONS

"Extraction of Blood Flow Information Using Doppler-Shifted Ultrasound", Halberg et al., Jun. 1986 Hewlett-Packard Journal, pp. 35–40.

"Digital Interpolation Beamforming for Low-Pass and Bandpass Signals", Pridham et al., Proceedings of the IEEE, vol. 67, No. 6, Jun. 1979, pp. 904–919.

"Explososcan: A parallel processing technique for high speed ultrasound imaging with linear phased arrays," Shattuck et al., J. Acoust. Soc. Am. 75 (4), Apr. 1984, pp. 1273–1282.

"A Digital Annular Array Prototype Scanner for Real-time Ultrasound Imaging", Foster et al., Ultrasound in Med. & Biol., vol. 15, No. 7, pp. 661–672, 1989.

*Primary Examiner*—Ian J. Lobo

[57] ABSTRACT

In accordance with the principles of the present invention, advantage is taken by the inventors of the fact that the speed of operation of the digital hardware in a digital beamformer can be reduced by providing, for example, multiple phases of the data signals and then processing the multi-phase data in N parallel summing paths. An interpolation-decimation filter receives the multiphase data from the N parallel summing paths and provides at its output a signal having a reduced data rate (1/N). In accordance with this technique, the speed of operation of the individual digital circuits for forming the required beamforming delays is not increased as compared to conventional post-beamforming interpolation schemes, so that hereby the effective data rate is increased by a factor N and results in a decrease of the delay quantization error by a factor N. In accordance with the principles of the invention, the interpolation-decimation filter is incorporated into the beamformer at a most advantageous place. That is, it is incorporated into the beamformer processing after partial beamforming of a group of receive channels and before formation of the final beam. This approach allows the final beamforming to be simple and performed at a relatively low data rate and allows the higher rate signal processing to be confined to circuitry which may advantageously be on a single type of integrated circuit which is repetitively used in the beamformer.

16 Claims, 7 Drawing Sheets

PARTIAL BEAMFORMING

CROSS REFERENCE TO RELATED APPLICATION

U.S. application Ser. No. 08/037,765 entitled DIGITAL BEAMFORMER HAVING MULTI-PHASE PARALLEL PROCESSING which is assigned to the same assignees as the instant application and filed concurrently herewith has related subject matter.

BACKGROUND OF THE INVENTION

1. Field of the Invention

This invention relates to a time-domain receive beamformer using digital signal processing techniques, i.e., analog to digital converters, digital memories, adders, multipliers, filters, etc., and more particularly, to a method and apparatus for digital receive beamforming in a medical ultrasound diagnostic system.

2. Background of the Invention

The objective of beamforming in a system is to form a narrow beam for improving reception of a signal arriving from a desired location, in the presence of noise and interfering signals from other locations. Beamforming can be performed during energy transmission or reception. This invention relates to the formation of beams during reception.

Beamforming is useful in a number of applications, i.e., radar, sonar, communications, geophysics, astrophysics, etc. The present invention concerns beamforming in ultrasound imaging. Using medical ultrasound imaging apparatus, anatomical structures within a body of a patient can be displayed and analyzed. The apparatus transmits sound waves of very high frequency (typically 2 MHz to 10 MHz) into the patient and then processes the echoes reflected from structures in the body being examined. The purpose of the apparatus is to display and/or analyze the return echoes. There are many types of displays used by medical ultrasound diagnostic apparatus, but probably the one most generally useful is a two-dimensional image of a selected cross-section of the anatomical structure being examined. This important mode of operation is called the echo or B mode. Using this mode of operation, a number of anatomical defects in a patient can be detected. Furthermore, the size of these defects can be more or less precisely determined. In this mode of operation all echoes from a selected cross-section are processed and displayed. The most critical operational parameter with respect to performance in this mode of operation is the size of the resolution cell. The size of the resolution cell can be decreased (thereby increasing resolution) by implementation of dynamic focusing and dynamic (matched) filtering. These techniques are easier to implement with a digital beamformer than with an analog beamformer.

In some clinical applications, anatomical defects can be relatively small and overshadowed by echoes reflected from larger anatomical structures. However, a small anatomical defect in or near a blood vessel may manifest itself by causing a relatively large change in the velocity of blood flowing in the vessel. It is known that a Doppler shift echo processing technique can be used for determining the velocity of a moving object. The display of Doppler shift for blood flow allows relatively small anatomical abnormalities to be more easily detected. This mode of operation, now commonly referred to as Color Flow, such as described in U.S. Pat. No. 4,800,891 issued to Kim, allows Doppler information about blood velocity to be gathered from large selected cross-sections of the anatomical structure. It is difficult, however, to acquire sufficient ultrasound data to develop an accurate high resolution blood flow image at a sufficiently high frame rate. In order to get more precise Doppler information about blood flow velocity from a small cross-section area, a Doppler processing technique such as known, for example, from an article by Halberg and Thiele published in the Hewlett-Packard Journal, pp. 35–40, June 1986, may be used. Using this technique it is possible to devote more time to a selected small area. The Doppler data is usually processed by FFT techniques and displayed by means of a spectrum. The Doppler data is also presented as an audio signal.

The quality of the beamforming has its greatest influence on the accuracy, resolution and other parameters of the forenoted modes of operation of the ultrasound imaging apparatus. A conventional beamformer electronically provides time delays to match the signal propagation delays of the ultrasound pressure field which is incident upon the ultrasound beamformer from a specific direction. This time-delay (or spatial processing) enhances the amplitude of the coherent wavefront relative to the background noise and directional interference. In an analog beamformer, this is done using analog delay lines and summing networks. These analog components restrict modern ultrasound diagnostic equipment in many different ways and are therefore undesirable. They are relatively expensive, unstable, and influenced by environmental conditions and age. Analog components also require careful manufacturing and assembly. The use of analog delay lines also limits the desired flexibility of modern ultrasound apparatus. Many compromises have to be made in an analog beamformer in order to support the previously mentioned major modes of operation. Furthermore, parallel processing, which is necessary for increasing the frame rates of real time ultrasound equipment, is very costly if the beamformer is implemented using analog processing techniques.

The increase of performance and reliability and decrease of cost of digital components makes digital beamforming a more promising alternative as compared to classical analog beamforming. Precision, stability and flexibility are the main advantages of digital signal processing techniques. The current standard digital circuitry can work at Nyquist rates exceeding 30 MHz. These sampling frequencies are high enough for RF sampling and temporal processing of modern ultrasound signals. However, the sampling rate required to properly match the propagation delays in a digital beamformer is several times greater than the Nyquist rate for accurate signal reconstructions, i.e., it is more than 100 MHz. These processing speeds, coupled with the required precision, are still above the performance levels of presently available analog-to-digital converters (ADCs). The remaining digital functions (e.g. other than the ADC's) can be performed at these speeds by parallel processing using standard digital components.

A method proposed by Pridham and Mucci, in an article published in Proceedings of the IEEE, Vol. 67, No. 6, pp. 904–919, June 1979, eases the high speed sampling requirement for ADCs in digital beamforming by the use of digital interpolation. The received echoes need only be sampled at an interval which satisfies or exceeds the Nyquist frequency, $f_0$. The price for this reduction in ADC sampling rate is a corresponding increase in the digital processing requirements. The fine delay increments necessary for beamforming are developed using digital interpolation. In digital interpolation, the data is first padded with zeros (e.g., zeros interspersed with the data), which effectively increases the data rate. At a later point in the processing, digital filters are used to reduce the data rate to its original value. Pridham and Mucci proposed two alternative approaches. In the first, a pre-beamforming interpolation approach, the zero padding circuitry and interpolation filters for each receive channel are placed after the ADC, but before the beamforming circuitry. In the second, a post-beamforming interpolation approach, the interpolation filter is placed after the beamforming. Filtering after beamforming is possible because beamforming is a linear operation. In the first approach, signal processing requirements are not optimal, since an interpolation filter is required for each received channel. In the second approach, the digital processing required for the interpolation filtering is reduced as compared with the required processing of the first approach since filtering is done only once rather than for each channel. The digital processing requirements can be further reduced by incorporating the interpolation filter into the digital filters of the receiver circuits which follow the digital beamformer. However, the beamforming signal processing is still not optimal because the beamformer processing rates (i.e., those needed to generate the required time delays) are much higher than the signal Nyquist rate.

It is an object of the present invention to provide a method and apparatus for digital beamforming which minimizes the signal processing rates in order that a system can be built with digital circuitry working at the signal Nyquist rate. Incorporation of such a method or apparatus in an ultrasound diagnostic system will offer all the advantages of digital beamforming, i.e., flexibility of the various modes of operation, parallel channel beamforming, dynamic focusing, matched filtering, etc, while minimizing the signal processing data rate.

SUMMARY OF THE INVENTION

In accordance with the principles of the present invention, advantage is taken by the inventors of the fact that the speed of operation of the digital hardware in a digital beamformer can be reduced by providing multiple phases of the signal data and then processing the multi-phase data in N parallel summing paths. In accordance with this technique, the speed of operation of the individual digital circuits for forming the required beamforming delays is not increased as compared to conventional post-beamforming interpolation schemes, so that hereby the effective data rate is increased by a factor N and results in a decrease of the delay quantization error by a factor N. Additionally, an interpolation-decimation filter is incorporated into the beamformer at a most advantageous place. That is, it is incorporated into the beamformer processing after partial beamforming of a group of receive channels and before formation of the final beam. This approach allows the final beamforming to be simple and performed at a relatively low data rate. Furthermore, with appropriate selection of the grouped received channels, the multi-phase data processing and subsequent interpolation can advantageously be confined to a single integrated circuit or circuit board.

These and other features and advantages of the invention will be apparent from the following description of the preferred embodiments and from the claims.

For a fuller understanding of the present invention, reference should now be made to the following detailed description of the preferred embodiments of the invention and the accompanying drawings.

DETAILED DESCRIPTION OF THE PREFERRED EMBODIMENTS

Modern medical ultrasound systems use probes having multiple transducer elements, and therefore have beamformers with multiple signal processing channels. The number of channels can be 64, 128, and even as high as 256. It is generally not practical to implement all of the beamformer signal processing channels on a single circuit board. Therefore, the receive beamformer is usually divided into several groups. Each group is a partial beamformer containing a number of receiving channels (e.g., eight or sixteen channels). The echo signal from a target is received by the transducer elements of a probe. Each element is connected to a different receiving channel. In each receiving channel the signal from a transducer element is amplified and then digitized at a uniform rate, $f_0$.

Figure 1:
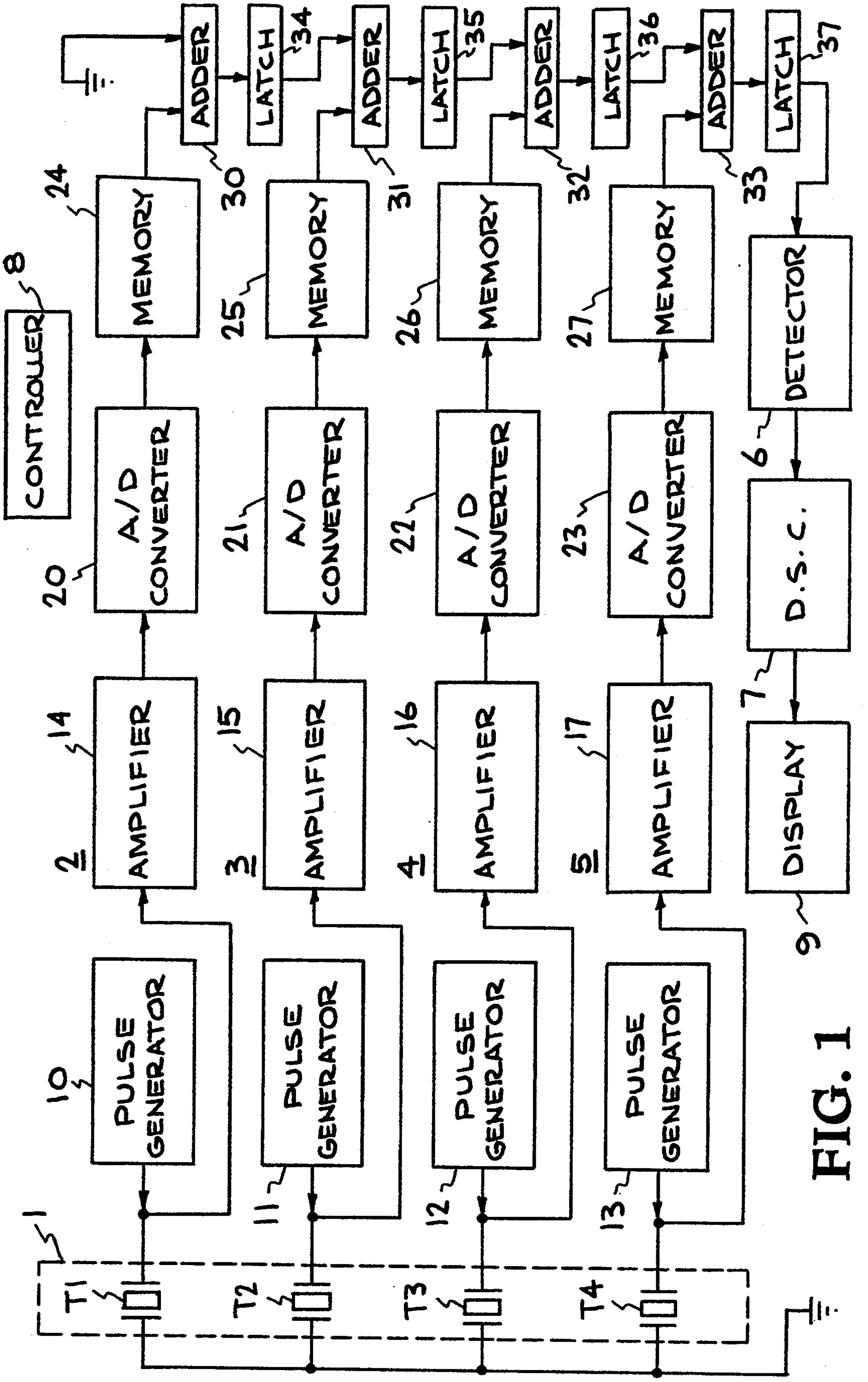
FIG. 1 illustrates in functional block diagram form, an ultrasound imaging apparatus in accordance with the prior art having a digital beamformer and serial summation of data samples from each receive channel.

An electronic scanning ultrasound diagnostic apparatus having a beamformer including a serial data summing path is shown in FIG. 1. An ultrasound probe 1 consists of an array of transducer elements T1 through TM. In order to simplify the description, it is assumed that M=4 although as noted above, it can be much greater. Four pulse generators 10 through 13 generate conventional driving pulses by means of trigger signals, as well known, to cause elements T1 through T4 to transmit ultrasound signals into the tissue of a body under test. Ultrasound echo signals which are reflected from within the tissue under test will be received by the same transducer elements T1 through T4. The signal developed from each element in response to the echoes is amplified by a respective one of amplifiers 14 through 17 and then digitized by a respective one of ADCs 20 through 23 at a uniform rate, $f_0$, in parallel receiving channels 2 through 5. The received digital data from the parallel receiving channels is stored in memories 24 through 27, respectively. The data read-out from memories 24 through 27 is serially added to the data from the preceding parallel receiving channel by a serial summation path including adders 30 through 33. The sums at the adder outputs are temporally stored by latches 34 through 37 before sending them to the next channel. In order to take into account and compensate for the signal processing time delays caused by the serial summation of the data by adders 30–33, time delays are developed by delaying the read-out or write-in of memories 24 through 27. The serial summation simplifies the signal processing data paths. The formed beam signal developed at the output of the last adder 33 is detected by a detector 6. In order to show the data on a display 9, it is necessary to convert the digital data signal into a video signal using a digital scan converter (DSC) 7, as well known.

Figure 2:
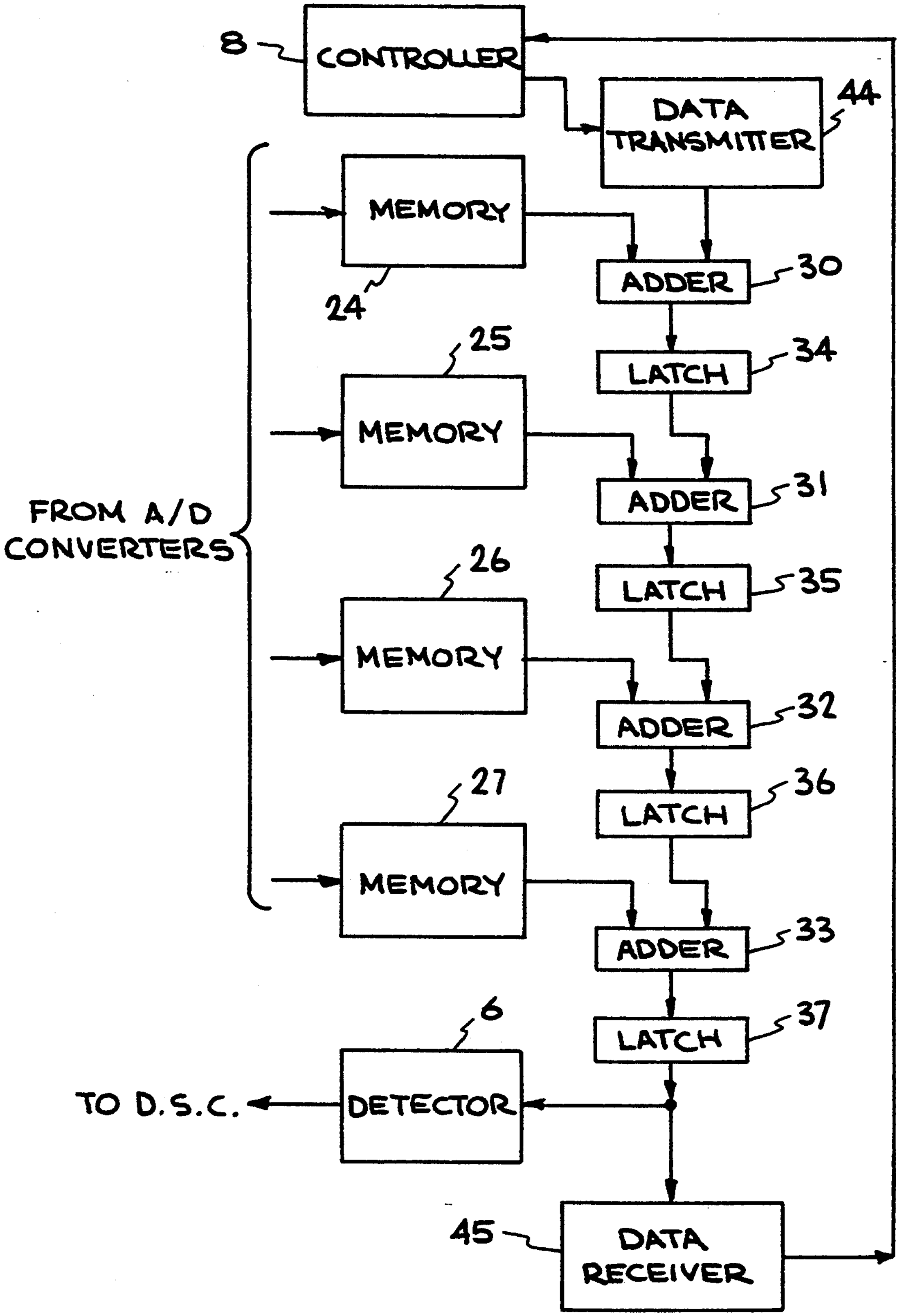
FIG. 2 illustrates in functional block diagram form the serial summation of data samples in the digital beamformer of FIG. 1, modified to include built-in testing circuitry.

As shown in FIG. 2, a built-in testing means is provided for each group of parallel receiving channels. A data transmitter 44 is connected at the beginning of the data summing path, and a data receiver 45 is connected at the end of the data summing path. Controller 8 sets a predetermined pattern of digital testing data for data transmitter 44 which is then processed by the data summing path and received by the data receiver 45. Controller 8 then analyzes the received data to see if it coincides with the expected data after the data summing. In the beamforming mode, zero's are generated by the data transmitter 44 in order that the serial summing of data from memories 24–27 is not disturbed.

To achieve a smaller quantization error for the dynamic focusing delay, in accordance with one aspect of the invention, a new beamformer interpolation arrangement is provided. In conventional beamformer interpolation, as previously stated, if the data rate is increased by a factor of N, then the processing speed of the adders and the clock frequency would increase by the same factor. To avoid the use of higher-frequency clocks and high speed adders, the new beamformer interpolation arrangement uses a multi-phase memory read-out scheme which 1) reduces the quantization error, and 2) allows the use of the same clock frequency, $f_0$, throughout the beamformer processing. With this arrangement, groups of the receive channels can be combined using a single interpolation-decimation filter, thereby forming a partial beam using each group of received channels.

Figure 3:
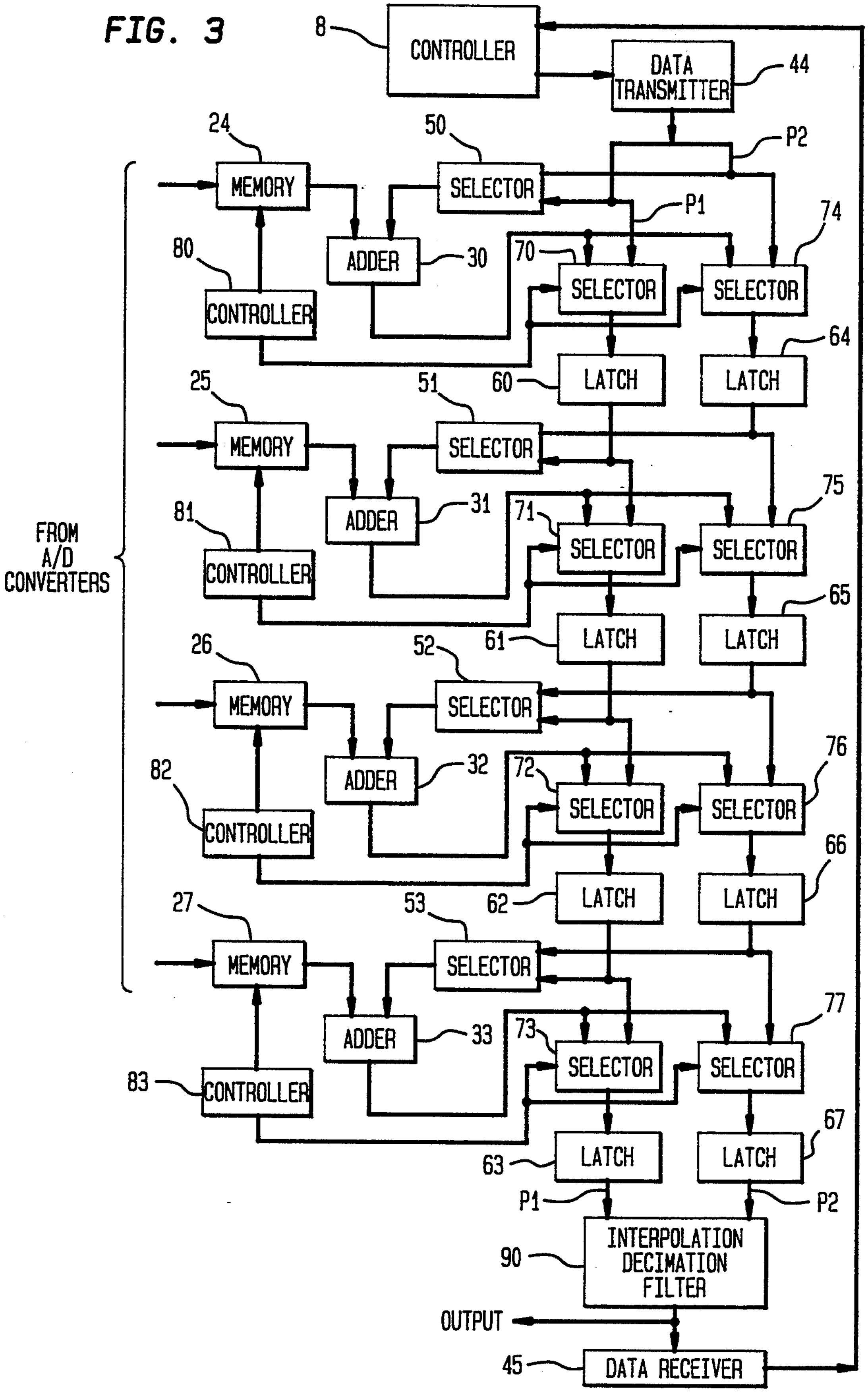
FIG. 3 illustrates in functional block diagram form, a novel multi-phase parallel processing scheme for a digital beamformer which, when compared with the embodiment of FIG. 1, illustrates novel apparatus for doubling the precision of the beamforming.

The new beamformer having a multi-phase memory read-out arrangement is illustrated in FIG. 3. The write-in data to memories 24 through 27 are clocked at the same rate as the sampling rate, i.e., $f_0$. The read-out clock is also $f_0$, but it is not uniform. Read-out is stopped at some clocks when an additional delay time is needed. This will give a delay time adjustment of $1/f_0$, referred to herein as a rough delay unit. To further reduce the quantization error of the delay time, the read-out data is sorted into N-parallel summing paths P1 and P2 (N=2 in FIG. 3), to fine tune the delay time to (n-1)/N of the rough delay unit, n=1, . . . , N. Each parallel summing path represents a different phase of the read-out data. Therefore, by shifting the read-out data to the next phase, the delay adjustment will be $1/(N f_0)$, referred to herein as a fine delay unit. By using the multi-phase read-out, the dynamic receiving focusing can be adjusted with fine delay units. Each data sample from a given channel is directed to only one of phases P1 and P2. However, before directing the data into the chosen parallel summing path, it is necessary to add it to the data sample from an adjacent channel. Selectors 70 through 77, 50 through 53, adders 30 through 33 and latches 60 through 67 execute directing and serial summation for the data samples provided to the parallel summing paths. For example, if data from memory 25 should be directed into phase P1, data from latch 60 out of phase P1 is brought through selector 51 to adder 31. At the same time selector 75 brings data from phase P2 out from latch 64 to latch 65. Next, selector 71 selects data from adder 31 and directs that data to latch 61. Controllers 80–83 decide into which of N phases the data from memories 25 through 27 should be directed and controls the selectors and latches associated therewith accordingly. An interpolation-decimation filter 90 combines the multi-phase data, and then outputs the combined data at the system clock rate, $f_0$, to the remainder of the ultrasound system.

Figure 4:
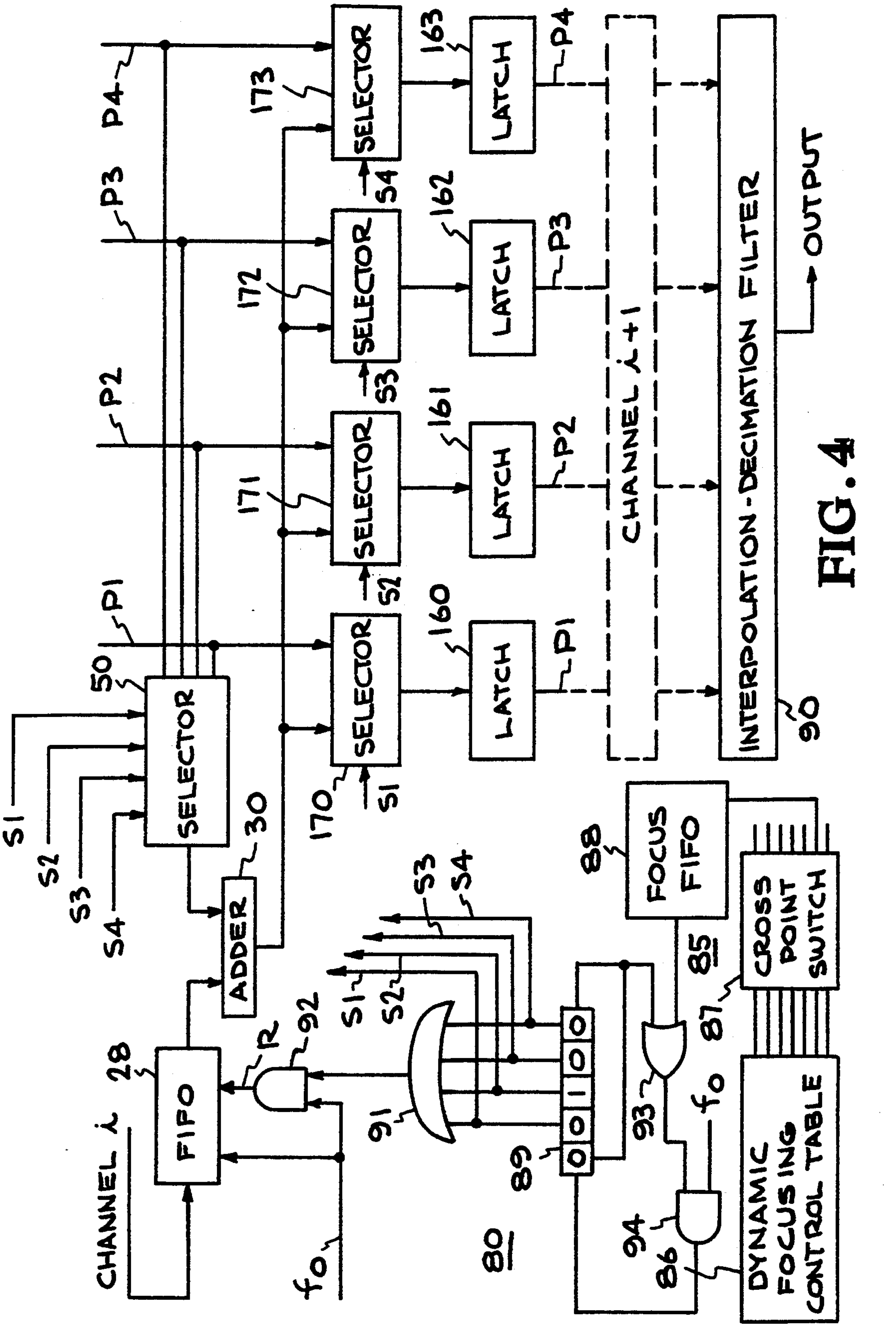
FIG. 4 illustrates in block diagram form details of a novel dynamic delay-time controller for a digital beamformer constructed as illustrated in FIG. 3, but having four-phase data and four parallel summing paths.

FIG. 4 is a preferred embodiment of a beamformer having four-phase data (P1 to P4) and thus four parallel summing paths for the echo data, and a dynamic delay-time controller 80. The dynamic delay time controller 80 outputs the phase information needed for each channel at each clock via memory read-out control signal R and selector control signals S1–S4. For example, if at a given time the memory read-out phase for a given channel is supposed to be at phase P2, the data on the P2 summing path from the preceding channels will pass through selector 50 and be added to the new data from channel i (when it is read out from FIFO memory 28) via adder 30. The sum from adder 30 will then go through selector 171 to the next parallel receiving channel (i+1). The remaining parallel summing paths (P1, P3 and P4) are directly connected via selectors 170, 172 and 173, latches 160, 162 and 163, which is equivalent to padding zero's to the ith channel echo data in these other phases. Thus, delay-time controller 80 controls the phase for each data sample read-out of each channel memory. A delay data memory 85, which may comprise a look-up table 86 for storing focusing delay data for all channels in the beamformer, a cross-point switch 87, and a shift register 88 (one shift register for each channel), outputs a 1-bit data stream for each channel. A '1' from the delay data memory 85, which is called a phase shift pulse, indicates that an additional fine delay time unit needed, and will cause an phase shift. A 5-bit shift-register 89 (one register for each parallel receiving channel), generates the phase information selector control signals S1–S4 and a memory read-out inhibit signal R is generated via an OR gate 91 and an $f_0$ clocked AND gate 92. Only one bit at a time in 5-bit register 89 is set to a '1' thereby indicating which of the four phases the data from the ith channel is to be directed. Whenever the shift register accepts such a phase shift pulse, the '1' shifts right-ward, thereby changing the selected phase from phase P1 to phase P2, or phase P2 to phase P3, or phase P3 to phase P4. An OR gate 93 and AND gate 94 are also coupled as shown between the output P4 of the shift register and its shift input. Thus, if there is no phase shift pulse from the delay data memory 85, the selector control signals (S1–S4) will remain unchanged. State 0 in the shift-register is a temporary state. When phase P4 is selected, the '1' increment shifts shift register from state 4 to state 0, temporarily. The next clock will change the state of the input to shift register 89 from state 0 to state 1. Shift register 89 will stay in state 1 until the next phase shift pulse '1' comes. During the clock period when the state is 0, data is not read-out from memory 28, and therefore the length of the delay for the data from memory 28 will be increased by 1. Thus, by this mechanism, the four fine delay units are turned into a rough delay unit.

The thus summed data in the four parallel summing paths in FIG. 4 are parallely provided to the input of interpolation-decimation filter 90. Filter 90 performs alignment, interpolation and decimation of the input data. Due to the multi-phase nature of the parallel input, the effective input data rate of filter 90 is four times greater than the data rate of the output or any of the input data from the parallel summing paths.

Figure 5:
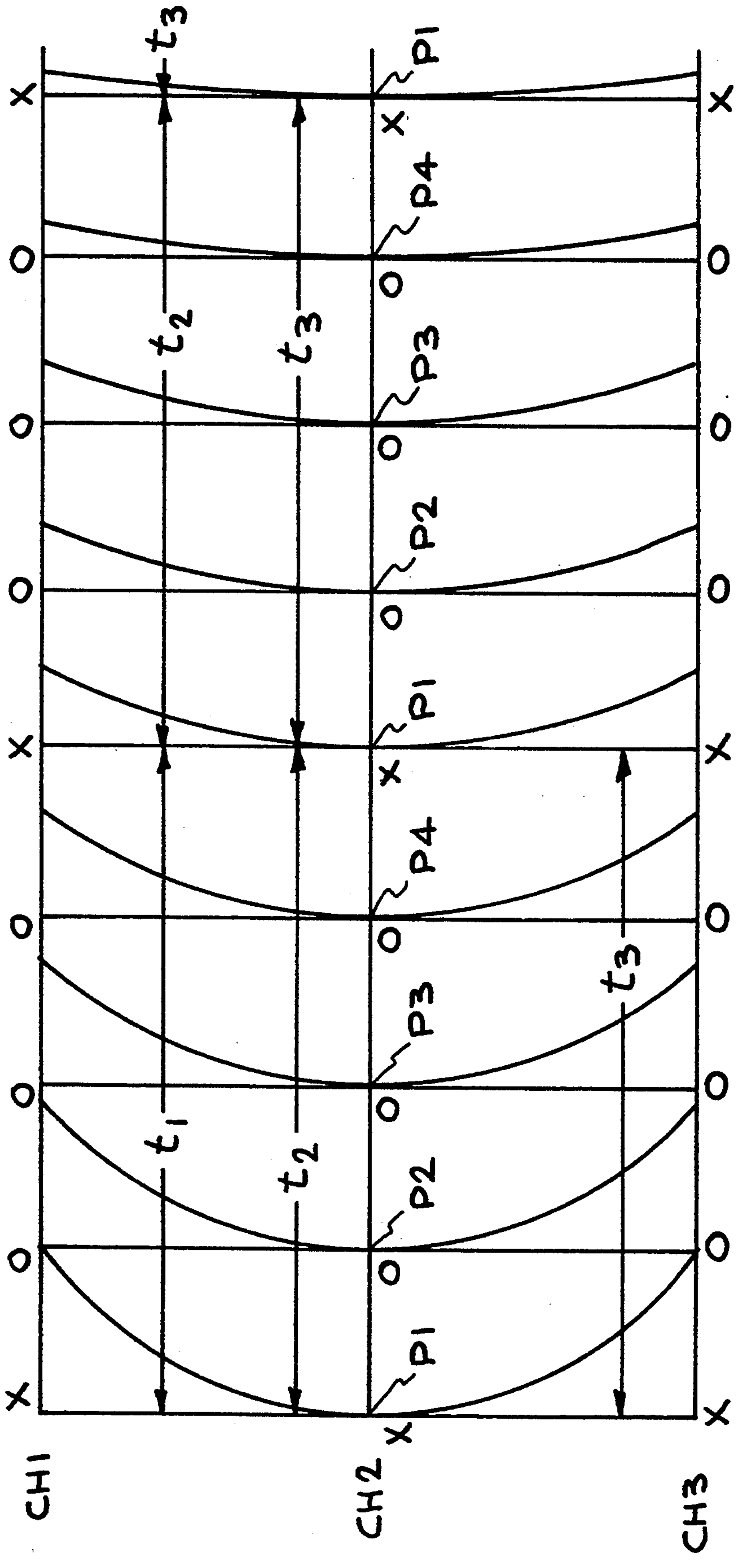
FIG. 5 graphically illustrates the assignment of successive N data samples for three adjacent receiving channels to various ones of the four phases shown in FIG. 4 for accomplishing beamforming.

FIG. 5 graphically illustrates, for purposes of example only, the assignment of three successive data samples for three adjacent receiving channels (1–3) to various ones of the four phases P1–P4 shown in FIG. 4, for three successive time intervals $t_1$, $t_2$ and $t_3$. In FIG. 5, actual data samples are denoted by an X (occurring at the $1/f_0$ rate), zero value samples for accomplishing zero padding are denoted by a 0 (occurring equally interspersed with the actual data samples at the $1/4f_0$ rate), and the horizontal direction is representative of time. For the three illustrated parallel receiving channels, the time delays required during each time period for achieving dynamic focusing of the beamformer is illustrated by the vertically oriented curved lines, as well known. It is obvious from this timing diagram that during the $t_1$ time interval for channel 1, only one actual sample (the second sample in channel 1) is closest to a time delay curve, the one just after the P4 phase, and therefore the P4 summing path is the most appropriate to receive this sample. For all other phases (P1 through P3) zeros are added to the data path (by the selector and latching circuitry of FIG. 4). During the time period between time intervals $t_1$ and $t_2$, the data from all four parallel summing paths are passed from channel 1 to channel 2 (by the selector and latching circuitry of FIG. 4). During time interval $t_2$ an actual data sample is read-out from the memory for receiving channel 2 and directed into the parallel summing path representing phase P1, since that actual sample is closest to the required time delay curve. At the same time ($t_2$), for channel 1, there is no actual sample which is closest to any of the time delay curves. Note, the actual sample (the third sample) is in fact closer to phase P1 for the $t_3$ time period. Thus, all four phases during the $t_2$ time period for channel 1 are zero padded. This "no data providing" corresponds to the above-noted state "0" of shift register 89. Next, between times $t_2$ and $t_3$, sample data are passed from receiving channel 2 to receiving channel 3 and from receiving channel 1 to receiving channel 2. During time $t_3$, the third sample read-out from the memory of channel 1 is placed into the parallel summing path representing phase P1 (as previously noted), the second sample read-out from the memory of channel 2 is placed into the parallel summing path representing phase P1, and the second sample read-out from the memory of channel 3 is placed into the parallel summing path representing phase P4.

Figure 6:
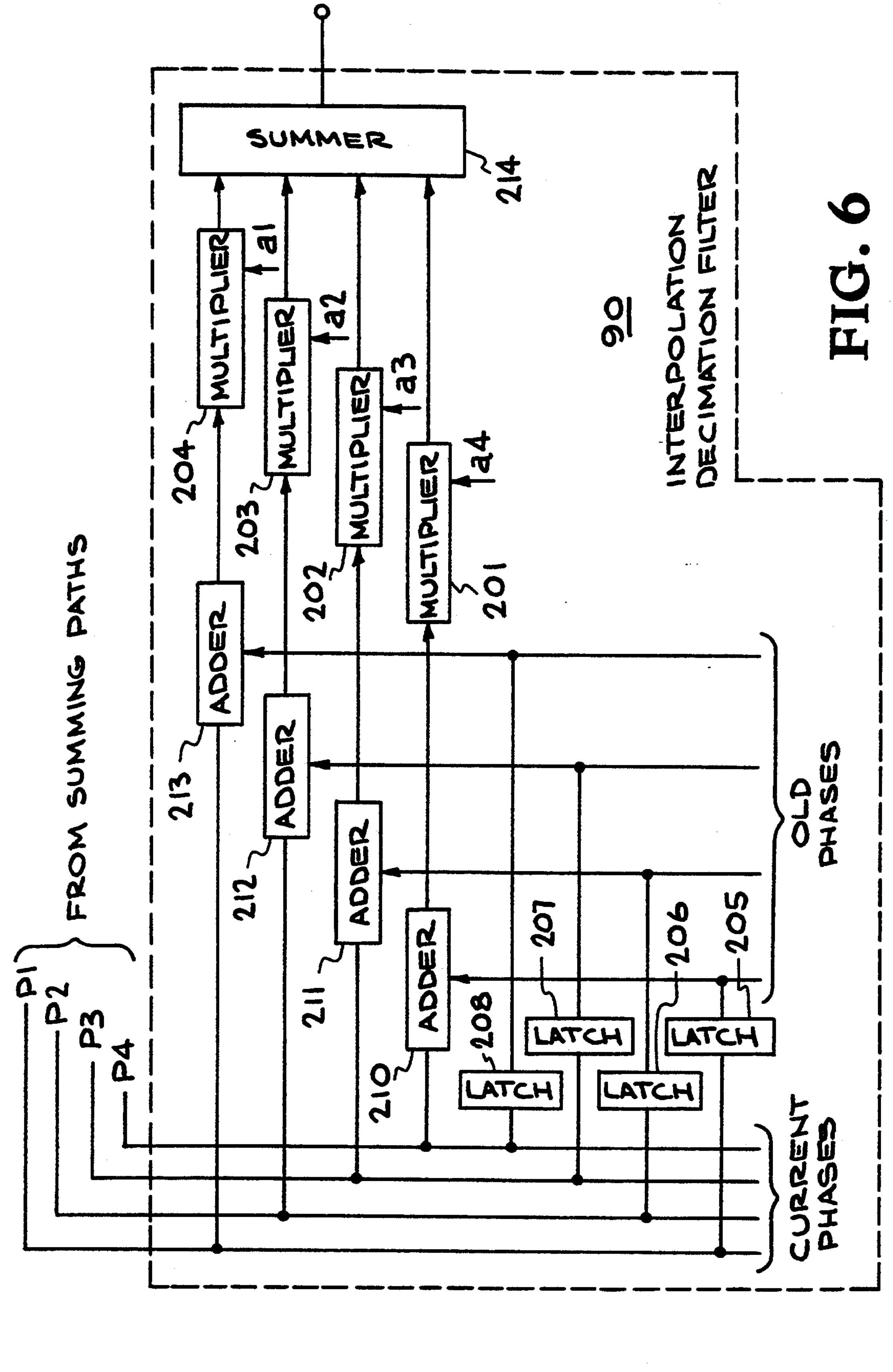
FIG. 6 illustrates in block diagram form details of an FIR filter constructed in accordance with the principles of the invention and used for the alignment, interpolation and decimation of data samples for the digital beamformer shown in FIG. 4.

In the preferred embodiment of the invention, it is convenient to use a Finite Impulse Response (FIR) filter for interpolation-decimation filter 90 because of its short transient response time and inherent linear phase. The FIR filter shown in FIG. 6 comprises (for a four-phase system) an 8-tap low pass filter and advantageously uses symmetric impulse response weighting coefficients (a1, a2, a3, a4; a4, a3, a2, a1) to save on the number of multipliers 201, 202, 203, and 204 required. The "current" phase data from the summing paths representing phases P1, P2, P3 and P4 are stored in latches 205, 206, 207, and 208, respectively, for forming "old" phase data. Then, the "old" phase data are appropriately added to the "current" data arriving on summing paths representing phases P4, P3, P2, and P1 via adders 213, 212, 211, and 210 and a final beamformer output sample is produced by combining the output of multipliers 201, 202, 203 and 204 in a summer 214.

It has been proposed by Pridham and Mucci, as noted above, that the interpolation and decimation filter can be placed before or after beamforming. Prebeamforming implementation of this filter requires that every channel has its own interpolation-decimation filter. While post-beamforming implementation solves that problem, it requires that beamforming has to be done at very high sample frequencies. In accordance with the principles of the invention, this filter is implemented during, rather than before or after, beamforming. This approach places the filter where it is the most cost effective for the architecture of the beamformer as a whole. The filtering and data rate reduction is performed after a partial beamforming of a group of several of the parallel receiving channels. For example, the parallel receiving channels can be combined into groups of two, four, eight or more. The filter can then be physically placed on the same board or integrated circuit (IC) used for the partial beamforming of the grouped channels. This technique reduces the number of interconnections and/or the data rate which are required between the grouped channels, circuit boards and IC's. Then, the final adding of the grouped channels (i.e., the partially formed beams) can be done at the system sampling rate and using only one data path.

Figure 7:
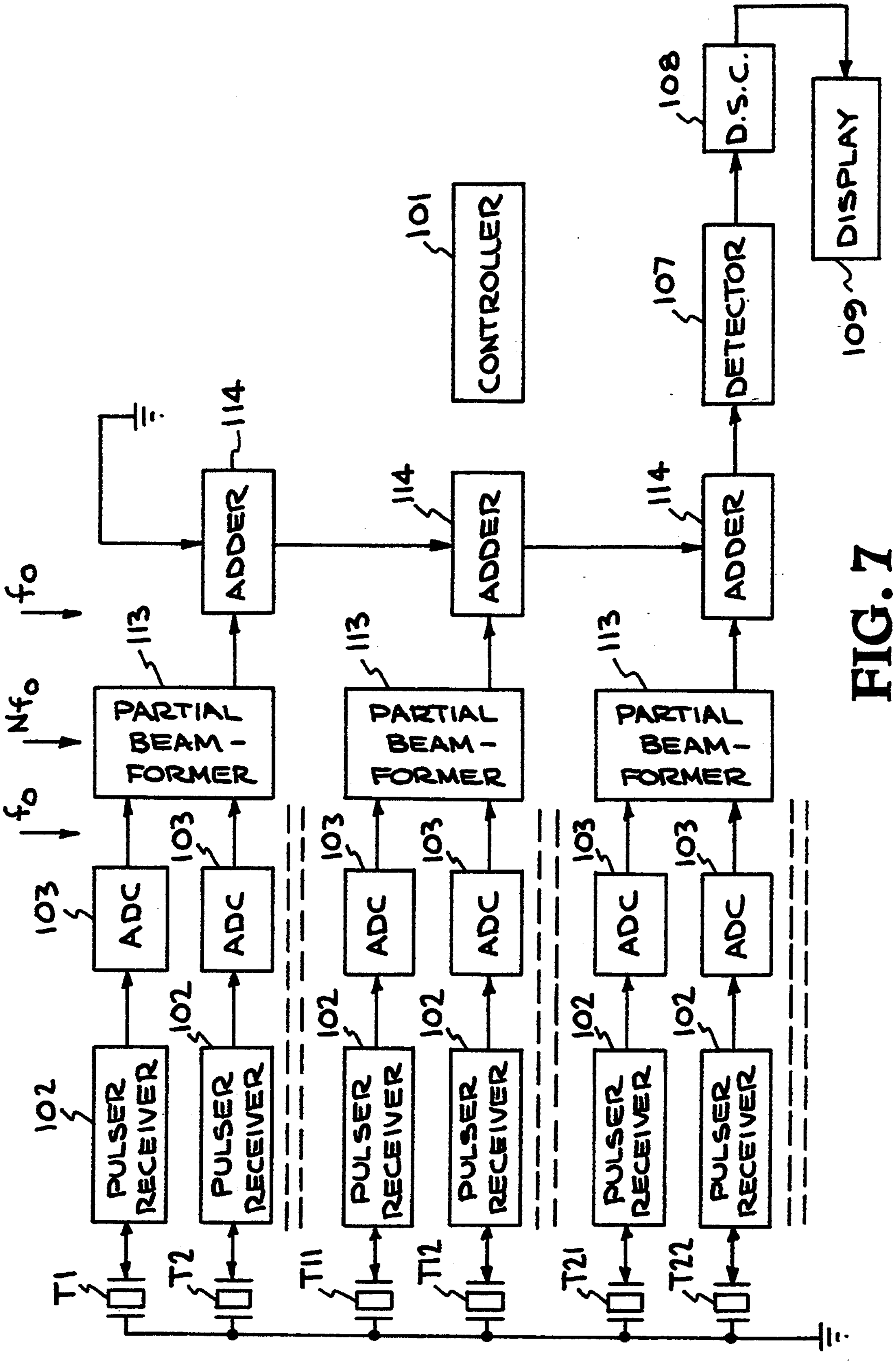
FIG. 7 illustrates in functional block diagram form, a digital beamformer constructed in accordance with a further aspect of the invention consisting of partial beamformers and serial summation of the signal samples from each partial beamformer.

FIG. 7 is the overall diagram of the receive beamformer which more clearly illustrates the partial beamforming aspect of the invention. In each channel, the echo signal from a target is received by the transducer elements of a probe. Each transducer element is connected to a pulse receiver 102 of conventional design. The signal developed by each transducer element is digitized with an ADC 103 at a uniform rate $f_0$, e.g. 36 MHz. Groups of adjacent parallel receive channels (e.g., 8) are combined so as to form a partial beamformer 113. In contrast with conventional prior art methods, the present invention provides an interpolation-decimation filter for each partial beamformer 113. Although it is possible to use only one interpolation-decimation filter for the whole beamformer system, the illustrated scheme has one interpolation-decimation filter per each group of receive channels, which reduces the data rate after partial beamforming to the sampling rate, $f_0$. That is, the signal processing rate of $f_0$ is used both before and after beamforming, but within the beamformer, the effective rate is, as shown in FIG. 4, four times $f_0$. From a hardware point of view this is an extremely advantageous implementation, since the high effective signal rates are confined to a single circuit board or even a single integrated circuit, thereby reducing system interconnects and complexity. The signals from the output of each partial beamformer 113 are then serially added using adders 114 (operating at $f_0$) to form the final beam. In order to take into account data delays due to serial adders 114, the delay values established at the outputs of memories 24–27 have an additional delay added for compensation purposes. The beam signal from the last adder 114 is then sent to a detector 107. A D.S.C. 108 performs digital scan conversion of this signal into a video signal for reproduction by display 109.

Thus, there has been shown and described a novel beamforming method and apparatus which satisfies all the objects and advantages sought therefore. Many changes, modifications, variations and other uses and applications of the subject invention will, however, become apparent to those skilled in the art after considering this specification and its accompanying drawings, which disclose preferred embodiments thereof. For example, less or more than four data summing paths can be used, and delay-time controller 80 could be accomplished using a variety of different techniques. Furthermore, each digital signal sample could be derived from two or more transducer elements, instead of one from each element. All such changes, modifications, variations and other uses and applications which do not depart from the spirit and scope of the invention are deemed to be covered by the invention which is limited only by the claims which follow.

We claim:

1. A beamformer, comprising:

a plurality of parallel receiving channels for detecting waves and, in response thereto, producing a respective plurality of digital sample signals comprising digital samples, and having a given sample rate ($f_0$), said plurality of receiving channels being comprised of a plurality of channel groups, each channel group being comprised of parallel receiving channels;

a plurality of partial beamforming means, each one of said plurality of partial beamforming means receiving the digital sample signals of one channel group of said plurality of parallel receiving channels, and processing said digital sample signals at a rate which is effectively a multiple (N) of said given rate ($f_0$) to develop an output of partial beamformer sample signals;

a plurality of filter means, each one of said filter means filtering the partial beamforming sample signals of a respective one of said partial beamforming means for developing a partial beamformer signal at said given rate ($f_0$); and a serial data adding path for adding together the partial beamformer signals of said given rate developed by each of said filter means, for forming a beamformer signal.

2. The beamformer of claim 1, wherein:

said partial beamforming means includes combining means for combining digital samples from said channel group of parallel receiving channels with appropriate time delays therebetween for accomplishing beam steering and/or dynamic focusing for developing said partial beamformer sample signals.

3. A beamformer, comprising:

a plurality of parallel receiving channels for detecting waves and, in response thereto, producing a respective plurality of digital sample signals comprising digital samples, and having a given sample rate ($f_0$), said plurality of receiving channels being comprised of a plurality of channel groups, each channel group being comprised of parallel receiving channels;

a plurality of partial beamforming means, each one of said plurality of partial beamforming means receiving the digital sample signals of one channel group of said plurality of parallel receiving channels, and processing said digital sample signals at a rate which is effectively a multiple (N) of said given rate ($f_0$) to develop an output of partial beamformer sample signals;

wherein said partial beamforming means includes combining means for combining digital samples from said channel group of parallel receiving channels with appropriate time delays therebetween for accomplishing beam steering and/or dynamic focusing for developing said partial beamformer sample signals; and wherein said partial beamformer means comprises means for adding zero value digital samples to said digital sample signals to provide a new digital sample signal, so as to increase the sample rate of said digital sample signals to said multiple (N) of said given rate ($f_0$);

a plurality of filter means, each one of said filter means filtering the partial beamforming sample signals of a respective one of said partial beamforming means for developing a partial beamformer sisal at said given rate ($f_0$); and a serial data adding path for adding together the partial beamformer signals of said given rate developed by each of said filter means, for forming a beamformer signal.

4. The beamformer of claim 3, wherein:

said filter comprises a digital interpolation/decimation filter.

5. The beamformer of claim 4, wherein:

said filter comprises a Finite Impulse Response (FIR) digital filter having symmetric impulse response weighting coefficients.

6. A beamformer, comprising:

a plurality of parallel receiving channels for detecting waves and, in response thereto, producing a respective plurality of digital sample signals comprising digital samples, and having a given sample rate ($f_0$), said plurality of receiving channels being comprised of a plurality of channel groups, each channel group being comprised of parallel receiving channels;

a plurality of partial beamforming means, each one of said plurality of partial beamforming means receiving the digital sample signals of one channel group of said plurality of parallel receiving channels, and processing said digital sample signals at a rate which is effectively a multiple (N) of said given rate ($f_0$) to develop an output of partial beamformer sample signals;

a plurality of filter means, each one of said filter means filtering the partial beamforming sample signals of a respective one of said partial beamforming means for developing a partial beamformer sisal at said given rate ($f_0$); and a serial data adding path for adding together the partial beamformer signals of said given rate developed by each of said filter means, for forming a beamformer signal;

wherein each partial beamforming means comprises:

a plurality of summing paths, each parallel summing path comprising a series connection of digital data adders and having an output;

delay determination means for determining for each digital sample of each digital signal, to which one of said parallel summing paths said digital sample is to be applied, said determination being based upon a time delay to be achieved between the digital samples of adjacent ones of said parallel receiving channels; and selective adding means responsive to said delay determination means for causing each digital sample of each of said plurality of receiving channels to be controllably added to said one parallel summing path determined for it, for forming added digital data samples in said parallel summing paths, said filter means being responsive to said added digital data samples.

7. The beamformer of claim 6, wherein:

said delay determination means includes calculation means for calculating a time delay needed between the digital samples of each receiving channel, so that when they are combined with the digital samples of the other receiving channels the output signals representative of wave reflection from a single point in said body are coherently added together in said parallel summing paths so as to form said beamformer signal.

8. The beamformer of claim 7, wherein:

said selective adding means includes a single adder for each of said parallel receiving channels, which adder is coupled by a multiplexing means and a latching means to each of said parallel summing paths; and said selective adding means controls said multiplexing means and said latching means so as to cause retrieval of a digital data sample from a given adder in said one parallel summing path, adding of said digital sample to said retrieved digital data sample for forming an added digital data sample, and then providing said added digital data sample to a point in said parallel summing path which follows said given adder.

9. The beamformer of claim 8, wherein:

said calculation means determines said time delays so as to achieve appropriate focusing and/or beam steering delays when said digital samples are added from said parallel receiving channels to said parallel summing paths.

10. The beamformer of claim 6, wherein:

said parallel receiving channels each include a digital storage device responsive to the digital samples in its channel, which storage device has either one or both of its write-in or read-out of the digital samples controlled so as to establish a rough time delay among digital sample signals of said parallel receiving channels.

11. The beamformer of claim 10, wherein:

said delay determination means determines a fine time delay among the digital samples of said parallel receiving channels depending upon which one of said plurality of parallel summing paths each one of said digital samples is to be applied, said fine time delay being quantized into time units of 1/N of said rough time delay units, where N is equal to the number of parallel summing paths.

12. The beamformer of claim 10, wherein:

said parallel summing paths comprise a series connection of adders and introduce an increasing delay to the added digital samples as they are processed therethrough, and said digital storage devices are controlled so as to establish a time delay among the digital sample signals of said parallel receiving channels which compensates for said increasing time delay.

13. The beamformer of claim 5, further including:

processor control means for providing control signals which control said delay determination means and said selective adding means, thereby controlling the adding of said added digital data samples in said parallel summing paths; and data transmitting means, responsive to said processor control means, for providing predetermined digital samples which are added to selective ones of said parallel summing paths, as controlled by said selective adding means, for developing added digital data samples in said parallel summing paths;

said processor control means being responsive to said added digital data samples of said parallel summing paths for analyzing said added digital data samples and comparing them to added digital data samples which are expected to be developed in said parallel summing paths in response to said predetermined digital samples provided to said parallel summing paths by said data transmitting means, thereby forming a built-in testing means for said beamformer.

14. The beamformer of claim 13, wherein:

said built-in testing means is controlled so as to individually test each one of said partial beamforming means.

15. The beamformer of claim 1, wherein:

the signal processing paths for each of said parallel receiving channels, partial beamforming means and filter means which is used for developing a single partial beamformer signal, are formed on a single circuit board.

16. The beamformer of claim 1, wherein:

the signal processing paths for each of said parallel receiving channels, partial beamforming means and filter means which is used for developing a single partial beamformer signal, are formed in a single integrated circuit.

* * * * *